(12) United States Patent
Han et al.

(10) Patent No.: US 8,367,367 B2
(45) Date of Patent: Feb. 5, 2013

(54) KIT FOR POSITIVELY DETECTING TOXIC MATERIAL

(75) Inventors: Jung-im Han, Yongin-si (KR); Soo-hyung Choi, Hwaseong-si (KR); Soo-suk Lee, Suwon-si (KR); Sung-ouk Jung, Suwon-si (KR); Joon-shik Park, Yongin-si (KR); Ki-eun Kim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 13/155,944

(22) Filed: Jun. 8, 2011

(65) Prior Publication Data

US 2011/0256570 A1   Oct. 20, 2011

Related U.S. Application Data

(62) Division of application No. 11/609,979, filed on Dec. 13, 2006, now Pat. No. 7,981,634.

(30) Foreign Application Priority Data

Jan. 19, 2006   (KR) .................. 10-2006-0005844

(51) Int. Cl.
*C12Q 1/26* (2006.01)
(52) U.S. Cl. ........................... 435/25; 435/975
(58) Field of Classification Search .............. 435/25, 435/975
See application file for complete search history.

(56) References Cited

U.S. PATENT DOCUMENTS

| | | | |
|---|---|---|---|
| 4,808,517 A | 2/1989 | Biondin et al. | |
| 5,278,048 A | 1/1994 | Parce et al. | |
| 5,372,784 A | 12/1994 | Morris et al. | |
| 5,843,696 A * | 12/1998 | Read et al. | 435/25 |
| 7,713,716 B2 * | 5/2010 | Han et al. | 435/25 |
| 7,981,634 B2 * | 7/2011 | Han et al. | 435/25 |
| 2007/0231919 A1 | 10/2007 | Choi et al. | |

OTHER PUBLICATIONS

Emanuele Argese, et al., "Quantitative structure-activity relationships for the toxicity of chlorophenols to mammalian submitochondrial particles", Chemosphere, vol. 38, No. 10. pp. 2281-2292, 1999.
European Search Report for Application No. 06124019.8-1223 dated Mar. 19, 2007.
A.S. Galkin, et al., "H+/2e in NADH quinone reductase reactions catalyzed by bovine heart submitochondrial particles", FEBS Letters (1999) 157-161.
Kurup, et al.,"The energy-linked nature of respiration-dependent bromothymol blue color decrease in submitochondrial partices", Biochim, Biophys. Acia, 189 (1969) 300-303.
L.M. Knobeloch, et al., Use of Submitochondrial particles for Prediction of chemical toxicity in man, Bull. Environ. Contam. Toxicol. (1990) 44:661-668.
Sue Hyung Choi, et al., "Phenolic toxicity-Detection and classification through the use of a recombinant bioluminescent *Escherichia coli*", Environmental Toxicology and Chemistry, vol. 20, No. 2, pp. 248-255 2001.

* cited by examiner

*Primary Examiner* — Ralph Gitomer
(74) *Attorney, Agent, or Firm* — Cantor Colburn LLP (57) ABSTRACT

A method of positively detecting toxic materials within a sample, the method including contacting sub-mitochondrial particles having competent mitochondrial enzymes formed from inner membranes of mitochondria, an electron donor which transmits electrons to an electron transfer system of the sub-mitochondrial particles and the sample, and forming reaction resultants, adjusting a pH of a pH indicator which change color according to a change in pH, adding the pH indicators to each reaction resultant and identifying color changes of the pH indicator. Also provided is a kit for positively detecting toxic materials within a sample.

5 Claims, 6 Drawing Sheets

| BEFORE TOXICITY REACTION | AFTER TOXICITY REACTION | | |
|---|---|---|---|
| A | TOXICITY | [A shaded] | : COLOR CHANGE |
| | NON-TOXICITY | [A] | : NO COLOR CHANGE |
| A B C D | NON-TOXICITY | [A] [B] [C] [D] | |
| | TOXICITY LEVEL 1 | [A shaded] [B] [C] [D] | |
| | TOXICITY LEVEL 2 | [A shaded] [B shaded] [C] [D] | |
| | TOXICITY LEVEL 3 | [A shaded] [B shaded] [C shaded] [D] | |

| | BEFORE TOXICITY REACTION (INITIAL pH=10) | AFTER TOXICITY REACTION |
|---|---|---|
| EXPERIMENTAL CONDITION | 0.0025% PHENOL RED | PHENOL RED (0.005%) :TOXICITY REACTANT=1:1 |
| NON TOXIC |  (CHERRY) |  (CHERRY) |
| 2.5% ETHANOL |  (CHERRY) |  (CHERRY) |
| 20% ETHANOL |  (CHERRY) |  (RED ORANGE) |

| EXPERIMENTAL CONDITION | BEFORE TOXICITY REACTION (INITIAL pH=10) PHENOLPHTHALEIN | AFTER TOXICITY REACTION PHENOLPHTHALEIN: TOXICITY REACTANT =1:1 |
|---|---|---|
| NON TOXIC | PINK | PINK |
| 2.5% ETHANOL | PINK | COLORLESS |

FIG. 7

| BEFORE TOXICITY REACTION | AFTER TOXICITY REACTION | | |
|---|---|---|---|
| PR PP <br> * PHENOL RED (PR) <br> * PHENOLPHTHALEIN (PP) | 20% EtOH | (RED ORANGE) PR | PP (COLORLESS) |
| | 2.5% EtOH | (CHERRY) PR | PP (COLORLESS) |
| | NON TOXIC | (CHERRY) PR | PP (PINK) |

KIT FOR POSITIVELY DETECTING TOXIC MATERIAL

This application is a divisional application of U.S. application Ser. No. 11/609,979, filed on Dec. 13, 2006 now U.S. Pat. No. 7,981,634, which claims priority to Korean Patent Application No. 10-2006-0005844, filed on Jan. 19, 2006, and all the benefits accruing therefrom under 35 U.S.C. §119, the contents of which in its entirety are herein incorporated by reference.

BACKGROUND OF THE INVENTION

1. Field of the Invention

The present invention relates to a method and a kit for positively detecting the presence of toxic materials within a sample and measuring the toxicity level thereof.

2. Description of the Related Art

Damage caused by an increase of hazardous materials due to industrialization such as environmental hormones, ecosystem damage caused by an increase of water pollution sources such as due to wastes and agricultural chemical components, damage caused by residual agricultural chemicals in food and heavy metal contamination in soil increasing on a daily basis, threaten human bodies and the environment.

Therefore, there is a need to monitor the harmfulness of chemical materials that may have negative influences on human bodies and the environment.

Various biological analysis methods for detecting toxic materials within environmental samples are known.

For example, U.S. Pat. No. 4,808,517 discloses an analysis method of toxic materials within an environmental sample including: mixing (a) a suspension of sub-mitochondrial particles having competent mitochondrial enzymes formed from inner membranes of mitochondria, (b) an analysis medium including a substrate in which either a substrate or an enzyme reaction product thereof may be detected using a spectroscopic detection method when the analysis medium is converted by mitochondrial enzymes, and (c) environmental samples in a common vessel, and determining how the sample influences enzyme activity within the suspension particles by measuring the changes of the substrate using spectroscopic measurement.

Such method can screen most toxic materials. However, since an instrument for spectroscopic measurement is required when applying that method, simplification of the method may not be possible. Also, the method cannot measure the toxicity levels of toxic materials. Also, such method is a negative detection method, which is different from a general positive detection mechanism, and thus, commercialization of the method is also not possible.

Figure 1A:
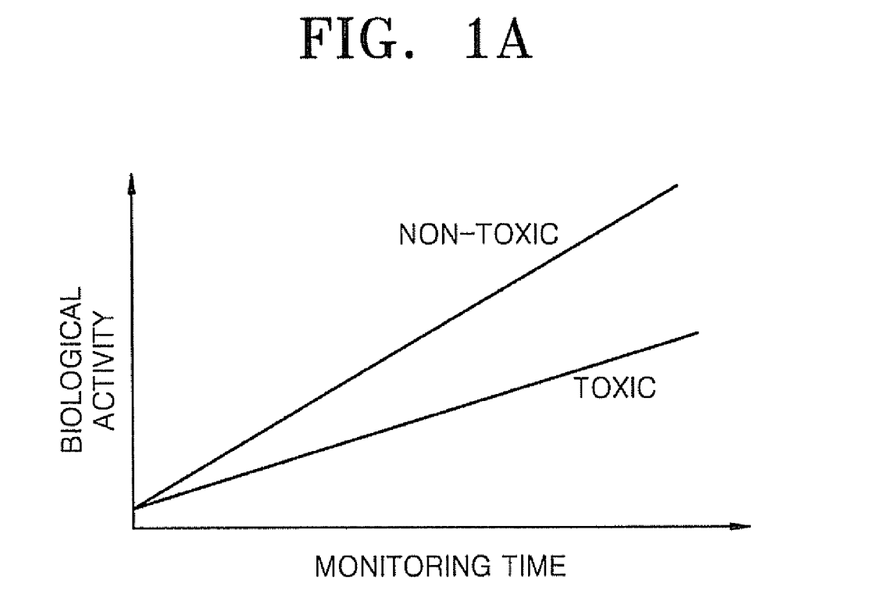
FIGS. 1A and 1B are graphs illustrating concepts for methods of negative detection and positive detection, respectively.
Figure 1B:
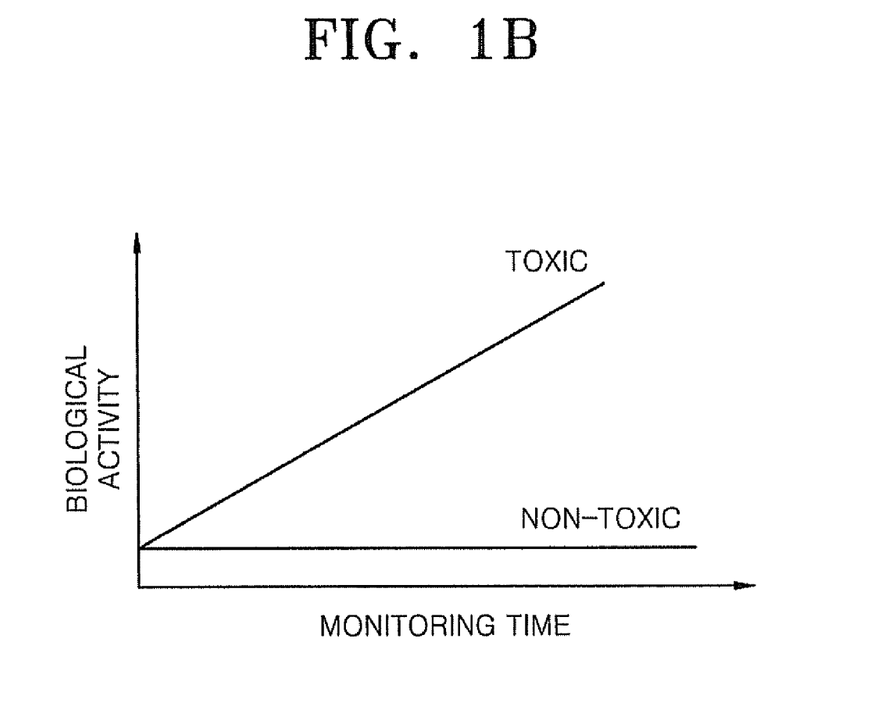

FIGS. 1A and 1B are graphs illustrating a concept for a method of negative detection and positive detection, respectively. Referring to FIG. 1A, negative detection measures the inhibition of a specific reaction caused by toxicity. Accordingly, small signal changes occur in the level of biological activity when toxicity exists due to the inhibition of the reaction. Conversely, significant signal changes occur in the level of biological activity when toxicity does not exist due to the absence of inhibition.

Referring to FIG. 1B, when a positive detection method is used, signal changes do not occur when toxicity does not exist and significant signal changes occur when toxicity does exist.

Some positive detection methods of detecting presence of toxic materials within a sample are known in the art. One example is a biosensor formed from a recombinant bioluminescent bacteria in which stress promoters and lux genes are transformed. Such biosensor generates a signal when specific toxic materials exist. (Sue-Hyung Choi and Man-Bock Gu, Phenolic Toxicity Detection and Classification Through the Use of a Recombinant Bioluminescent Escherichia, ENVIRONMENTAL TOXICOLOGY AND CHEMISTRY 2001: Vol. 20, No. 2, pp. 248-255).

However, such biosensors are selective when detecting specific toxic materials and detect toxic materials that cause certain stress. Thus not all of the various kinds of toxic materials can be screened, and accordingly, not all toxicity levels can be measured.

BRIEF SUMMARY OF THE INVENTION

An exemplary embodiment provides a method of positively detecting a number of toxic materials and measuring the toxicity level thereof.

An exemplary embodiment provides a kit for positively detecting a number of toxic materials and measuring the toxicity level thereof.

An exemplary embodiment of a method provides a method of positively detecting toxic materials within a sample. The method includes contacting sub-mitochondrial particles including competent mitochondrial enzymes formed from inner membranes of mitochondria, an electron donor transmitting electrons to an electron transfer system of the sub-mitochondrial particles and the sample, adjusting a pH of a pH indicator which changes color according to a pH change, the contacting forming reaction resultants adding the pH indicator to each reaction resultant and identifying color changes of the pH indicator.

In an exemplary embodiment, the sub-mitochondrial particles may be manufactured by sonicating whole mitochondria so that cristae transform to micelles.

In an exemplary embodiment, the mitochondrial enzymes may be formed of NADH-dehydrogenase, coenzyme-Q-cytochrome C reductase and cytochrome C oxidase.

In an exemplary embodiment, the electron donor may include one of reduced nicotinamide-adenine dinucleotide (NADH) and reduced nicotinamide-adenine dinucleotide phosphate (NADPH).

In an exemplary embodiment, the pH indicator may change color in a pH range of about 5.2 to 10.

In an exemplary embodiment, the pH indicator may be one of bromocresol purple, bromothymol blue, phenol red, thymolblue, phenolphthalein and a combination including at least one of the foregoing.

In an exemplary embodiment, the pH indicator may be adjusted in a pH range of about 7.5 to 11.

In an exemplary embodiment, the pH indicator may be adjusted in a pH range of about 9 to 11.

In an exemplary embodiment, the toxicity may be determined when the color of a pH indicator changes and non-toxicity may be determined when the color of a pH indicator does not change.

In an exemplary embodiment, the pH indicator may include at least two pH indicators and the identifying color changes includes measuring toxicity levels of toxic materials according to the color changes of the at least two pH indicators.

In another exemplary embodiment, there is provided a kit for positively detecting toxic materials within a sample. The kit includes sub-mitochondrial particles having competent mitochondrial enzymes formed from inner membranes of mitochondria, an electron donor transmitting electrons to an electron transfer system of the sub-mitochondrial particles and a pH indicator adjusting the pH thereof.

In an exemplary embodiment, the sub-mitochondrial particles may be manufactured by sonicating whole mitochondria so that cristae transform to micelles.

In an exemplary embodiment, the sub-mitochondrial particles may be lyophilized.

In an exemplary embodiment, the mitochondrial enzymes may be formed of NADH-dehydrogenase, coenzyme-Q-cytochrome C reductase, and cytochrome C oxidase.

In an exemplary embodiment, the electron donor may include one of NADH and NADPH.

In an exemplary embodiment, the pH indicator may change color in a pH range of about 5.2 to 10.

In an exemplary embodiment, the pH indicator may be one of bromocresol purple, bromothymol blue, phenol red, thymolblue phenolphthalein and a combination including at least one of the foregoing.

In an exemplary embodiment, the pH indicator may be adjusted in a pH range of about 7.5 to 10.

In an exemplary embodiment, the pH indicator may be adjusted in a pH range of about 9 to 10.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The invention now will be described more fully hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The term "competent enzyme" indicates an enzyme that is active in an mitochondrial electron transfer system.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. An exemplary embodiment of a method of positive detection detects various types of toxic materials and measures the toxicity level thereof.

In an exemplary embodiment, the method of detecting the presence of toxic materials within a sample includes a process of contacting sub-mitochondrial particles ("SMPs") having competent mitochondrial enzymes formed from the inner membranes of mitochondria, an electron donor which transmits electrons to an electron transfer system of the sub-mitochondrial particles, and a sample to be tested.

The sub-mitochondrial particles ("SMPs") may be lipid bilayer membrane vesicles obtained by a micro-formation from a fraction of a crista film when mitochondria are ruptured. Whole mitochondria derived from an arbitrary origin may be ruptured by an ultrasonic wave, a digitonin, or a french press process. Then, membrane fractions may be separated from cytoplasm residue by centrifugal separation. Then the membrane fractions are allowed to transform into vesicles which model the stable movements of the inner mitochondrial membrane. Such sub-mitochondrial particles can model movements of whole mitochondria and a large amount of sub-mitochondrial particles can be saved by being frozen or lyophilized after manufacturing. Thus, an aliquot of a sub-mitochondrial particle product can be relatively easily used in performing a toxicant assay, which may take an extended time period.

In an exemplary embodiment, the sub-mitochondrial particles may be manufactured by sonicating whole mitochondria so that cristae maytransform to micelles.

Exemplary embodiments of the sub-mitochondrial particles used in an can be manufactured by any of a number of methods or can be purchased commercially. In one exemplary embodiment, whole mitochondria are prepared. Mitochondria derived from an arbitrary origin may be used. The sub-mitochondrial particles may be manufactured from fresh mitochondria or from frozen mitochondria. Once the sub-mitochondrial particles are manufactured, they can be saved in a preserved mixture at about −20° C. Also, for a storage purposes, the sub-mitochondrial particles can be lyophilized. In order to use the lyophilized sub-mitochondrial particles in the method of the present invention, the lyophilized sub-mitochondrial particles can simply be defrosted. Lyophilized product can be saturated with an analyzing medium before use and thus can be relatively simply transformed. The sub-mitochondrial particles include competent mitochondrial enzymes.

As used herein, the term "competent mitochondrial enzyme" means that the enzyme involved in an electron transfer system of mitochondria is active. Accordingly, an exemplary method measures the extent of the effects of toxic materials on the electron transfer system of mitochondria or on an electron transfer system of sub-mitochondrial particles by detecting color changes. In more detail, toxic materials affect the enzymes of the electron transfer system of sub-mitochondrial particles, and thus, affect the amount of electrons transmitted from an electron donor to the electron transfer system of the mitochondria. Consequently, toxic materials affect the amount of electron donors within a reaction solution. An exemplary embodiment of a method measures the amount of electron donors within a reaction solution by detecting color change, and thereby measures the influences on the electron transfer system, including the extent of toxicity. However, the application of the method should not be considered as limited to the effect of toxic materials.

In an exemplary embodiment, the mitochondrial enzymes may be formed of NADH-dehydrogenase, coenzyme-Q-cytochrome C reductase, and cytochrome C oxidase.

In an exemplary embodiment, the electron donor may include at least one selected from the group consisting of NADH and NADPH.

In an exemplary embodiment, the toxic materials may include any of a number of toxic materials that may have an influence on the electron transfer system of mitochondria or sub-mitochondrial particles. Exemplary toxic materials include, but are not limited to, ethanol, methanol, phenols, heavy metals, and solvents.

The exemplary method of contacting described above can be performed under any of a number of conditions, such as a physiological condition or a condition similar to a physiological condition, as long as the enzymes of the electron transfer system can react in that condition. In an exemplary embodiment, contacting may be performed in a solution having physiological salt and ionic strength of a pH of about 7, such as in a phosphate buffered saline ("PBS" solution) or in another buffer, for a predetermined time. When contacting is performed under the physiological condition or in a solution similar to such physiological condition, the amount of the sub-mitochondrial particles may be about 0.1 to 0.5 milligrams per milliliter (mg/ml) and the amount of the electron donors may be about 1 to 30 millimoles (mM). As the concentration of the sub-mitochondrial particles and the electron donors increase, the reaction speed increases accordingly. Thus, the sub-mitochondrial particles and the electron donors may be used by considering the desired reaction speed and appropriately adjusting the concentration . . . .

In an exemplary embodiment, a method of detecting the presence of toxic materials within a sample includes a process of adjusting the pH of one or more pH indicators, which change color according to pH changes.

The pH indicator of the present invention may be any of a number of indicators as long as their color changes according to pH changes. In exemplary embodiments, pH indicators that may be used in the present invention are illustrated in Table 1.

TABLE 1

| Indicator | Color at low pH | pH range of color change | Color at high pH |
|---|---|---|---|
| Methyl violet | Yellow | 0.0~1.6 | Blue-purple |
| Thiol blue (first color change) | Red | 1.2~2.8 | Yellow |
| Methyl yellow | Red | 2.9~4.0 | Yellow |
| Bromophenol blue | Yellow | 3.0~4.6 | Purple |
| Congo red | Blue | 3.0~5.2 | Red |
| Methyl orange | Red | 3.1~4.4 | Yellow |
| Litmus | Red | 4.5~8.3 | Blue |
| Bromocresol purple | Yellow | 5.2~6.8 | Purple |
| Bromothymol blue | Yellow | 6.0~7.6 | Blue |
| Phenol red | Yellow | 6.6~8.0 | Red |
| Thymolblue (second color change) | Yellow | 8.0~9.6 | Blue |
| Phenolphthalein | Colorless | 8.2~10.0 | Pink |
| Thymolphthalein | Colorless | 9.4~10.6 | Blue |
| Alizarin yellow R | Yellow | 10.1~12.0 | Red |
| Indigo carmine | Blue | 11.4~13.0 | Yellow |

In an exemplary embodiment, the pH indicators may change color in the pH range of about 5.2 to 10.

In an exemplary embodiment, the pH indicators may be selected from the group consisting of bromocresol purple, bromothymol blue, phenol red, thymolblue, and phenolphthaleinn.

The pH of the one or more pH indicators may be adjusted by any of a number of methods. In one exemplary embodiment, the pH indicators may be adjusted by adding an acid or basic solution into the one or more pH indicators.

In an exemplary embodiment, the adjustment of pH indicators may be performed in the pH range of about 7.5 to 11. In one exemplary embodiment, the adjustment of pH indicators may be performed in the pH range of about 9 to 11.

In an exemplary embodiment a method of detecting the presence of toxic materials within a sample includes a process of adding one or more pH indicators to each reaction resultant.

The weight ratio of the reaction resultant to the pH-adjusted indicators is not particularly restricted and may be about 1:0.1 to 1:10. In exemplary embodiments, the weight ratio of the reaction resultant to the pH adjusted indicators may be 1:0.2 to 1:5. In one exemplary embodiment, the adjustment of pH indicators may be performed in the pH range of about 1:1.

In an exemplary embodiment, a method of detecting the presence of toxic materials within a sample includes a process of identifying color changes of the one or more pH indicators.

In an exemplary embodiment, when there are changes in the colors of the pH indicators, the sample may be identified as being toxic. Conversely, when there are no color changes in the pH indicators, the sample may be identified as being non-toxic.

In an exemplary embodiment, one or more pH indicators may be formed of at least two pH indicators and the toxicity level of toxic materials may be measured according to the combination of the color changes in these pH indicators.

Figure 2:
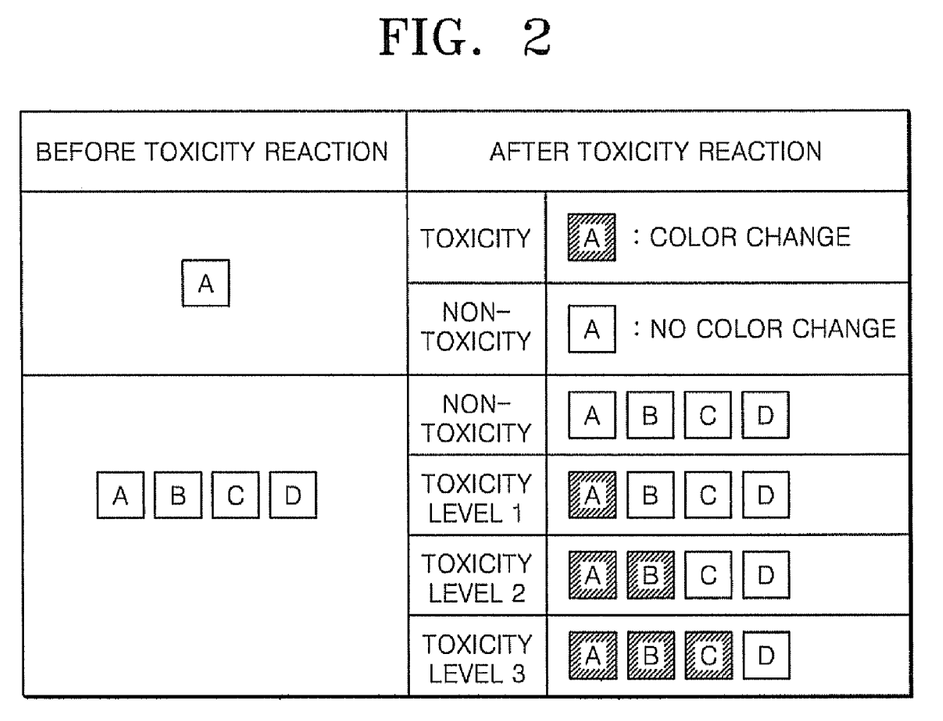
FIG. 2 is a schematic diagram illustrating an exemplary embodiment of a concept for a method of positively detecting toxic materials according to the present invention.

FIG. 2 is a schematic diagram illustrating an exemplary embodiment of a concept for a method of positively detecting toxic materials according to the present invention. Referring to FIG. 2, cases of using one pH indicator and using four pH indicators are illustrated.

In case where one pH indicator is used (e.g., [A]), when toxic materials exist in a sample, the color of the sample changes after the toxic reaction. Conversely, when toxic materials do not exist in a sample, the color of the sample does not change.

When using four pH indicators (e.g., [A], [B], [C], [D]), when toxic materials do not exist in a sample, the color of the sample does not change after the toxic reaction. Conversely, when toxic materials exist in the sample, a certain number of pH indicators may change their color according to the toxicity level of the sample.

When the toxicity level is low at 1, medium at 2, and high at 3, among four pH indicators, color changes occur in pH indicators A, pH indicators A and B, pH indicators and A, B, and C, respectively.

Figure 3A:
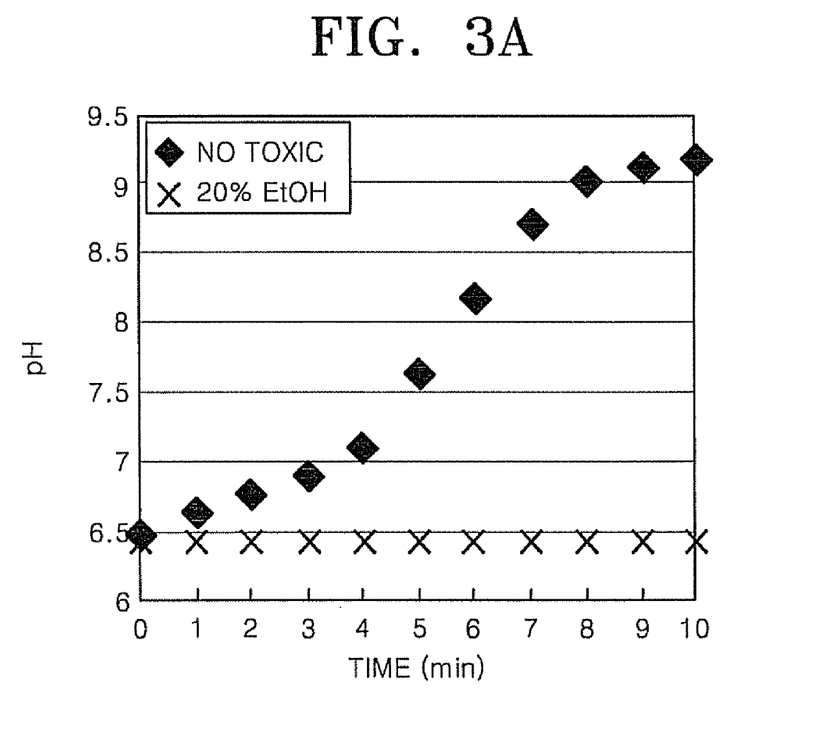
FIG. 3A is a graph illustrating changes in the pH values at one-minute intervals when 20 weight percent (wt %) of ethanol (toxic material) and 20 wt % of sorbitol (non-toxic material) are added to sub-mitochondrial particles and an electron donor.
Figure 3B:
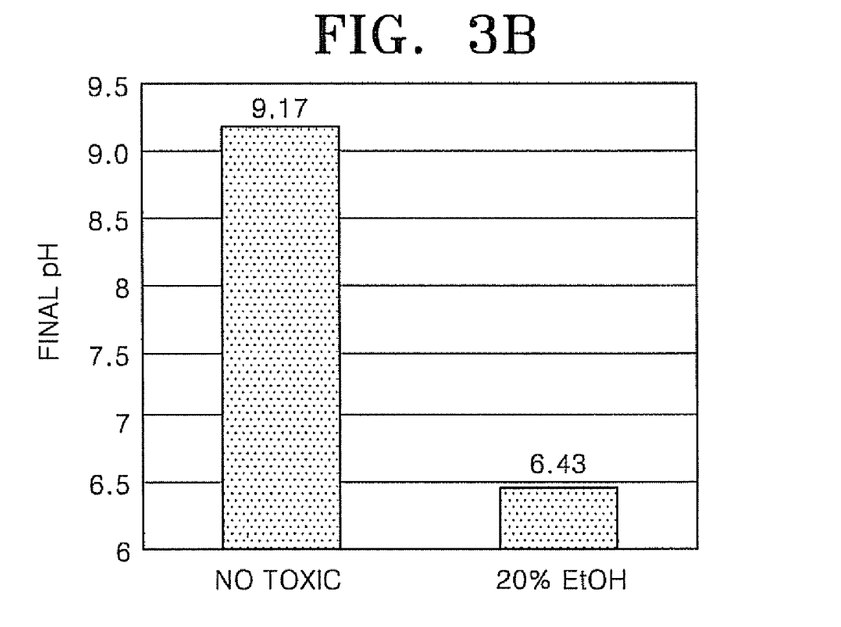
FIG. 3B shows the final pH values of each reactant 10 minutes after the reaction described in FIG. 3A was initiated.

FIG. 3A is a graph illustrating the pH values at one-minute intervals when 20 wt % of ethanol, (toxic material) and 20 wt % of sorbitol (non-toxic material) are added to sub-mitochondrial particles and an electron donor to cause reactions. FIG. 3B shows the final pH value of each of the reactant resultants after the reaction solutions were allowed to react for 10 minutes according to the reaction described in FIG. 3A.

Referring to FIGS. 3A and 3B, when toxicity exists in the sample, the pH starts at about 6.4 and 10 minutes later, the final pH of the reaction resultant becomes 6.43, showing little change. When toxicity does not exist in the sample, the final pH of the reaction resultant is rapidly increased to 9.17.

Using the result described above, an exemplary method of positive detection using phenol red as a pH indicator is now described. After phenol red is adjusted to various pH ranges, phenol red is added to the reaction resultant so that color changes may be identified and thus, toxic materials within a sample may be detected.

The values calculated from the above process using phenol red are illustrated in Table 2. The pH of the reaction resultants having toxic materials and non-toxic materials are assumed to be 6.3 and 9.3, respectively.

Referring to Table 2, when the initial pH of phenol red is adjusted to over 9, a signal (e.g., color after mixing) is essentially the same as the color before mixing when there are no toxic materials and the signal (e.g., color after mixing) is changed when there are toxic materials, indicating a positive mechanism.

TABLE 2

| Adjusted pH | Color before mixing | Mixed with 1:1 | [H+] | pH | Color after mixing |
| --- | --- | --- | --- | --- | --- |
| PH 7 | Red | pH 7 + pH 6.3 (toxicity) | $3.01 \times 10^{-7}$ | 6.52 | Red orange |
| | | pH 7 + pH 9.3 (non-toxicity) | $5.03 \times 10^{-8}$ | 7.30 | Red |
| PH 8 | Red | pH 8 + pH 6.3 (toxicity) | $2.56 \times 10^{-7}$ | 6.59 | Red orange |
| | | pH 8 + pH 9.3 (non-toxicity) | $5.25 \times 10^{-9}$ | 8.28 | Cherry |
| PH 9 | Cherry | pH 9 + pH 6.3 (toxicity) | $2.51 \times 10^{-7}$ | 6.60 | Red orange |
| | | pH 9 + pH 9.3 (non-toxicity) | $7.51 \times 10^{-10}$ | 9.12 | Cherry |
| pH 10 | Cherry | pH 10 + pH 6.3 (toxicity) | $2.51 \times 10^{-7}$ | 6.60 | Red orange |
| | | pH 10 + pH 9.3 (non-toxicity) | $3.01 \times 10^{-10}$ | 9.52 | Cherry |
| pH 11 | Cherry | pH 11 + pH 6.3 (toxicity) | $2.51 \times 10^{-7}$ | 6.60 | Red orange |
| | | pH 11 + pH 9.3 (non-toxicity) | $2.56 \times 10^{-10}$ | 9.59 | Cherry |

In order to verify the calculations illustrated above, actual experiments are conducted using an exemplary embodiment according to the present invention.

Figure 4:
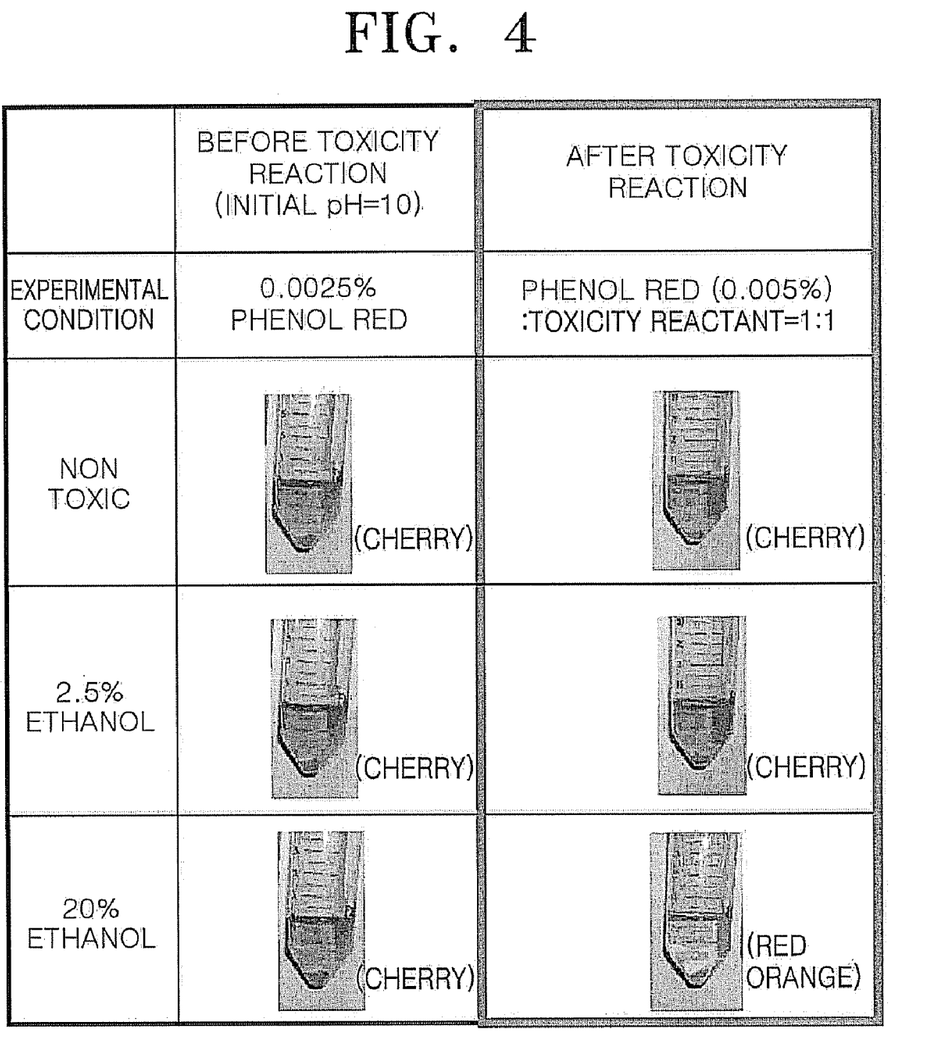
FIG. 4 is a diagram schematically illustrating an exemplary embodiment of the method of positively detecting toxic materials in which phenol red is used as a pH indicator according to the present invention.

FIG. 4 is a diagram schematically illustrating an exemplary embodiment of a method of positively detecting toxic materials in which phenol red is used as a pH indicator. Referring to FIG. 4, after the pH of phenol red was adjusted to 10 and mixed with the reaction resultant, the color did not change when toxic materials were not contained in the reaction resultant or toxic materials, e.g., 2.5 wt % of ethanol were contained in the reaction resultant. However, when highly toxic materials, e.g., 20 wt % of ethanol, were contained in the reaction resultant, the color changed after the toxicity reaction from the color before the toxicity reaction.

When phenol red is used, the presence of toxic materials can be positively detected. However, as low toxicity and non-toxicity produce the same result as shown above low toxicity levels cannot be measured.

Figure 5A:
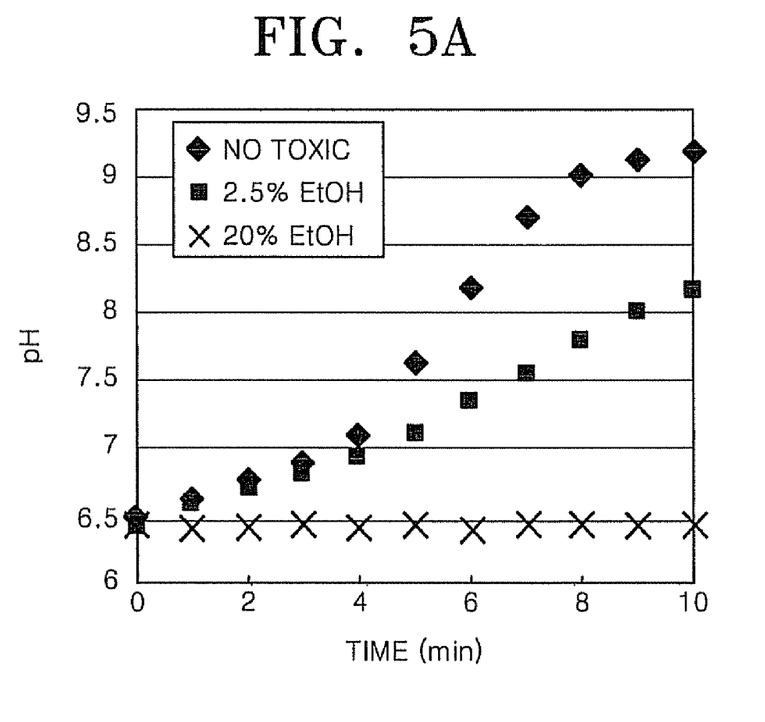
FIG. 5A is a graph illustrating the pH values at two-minute intervals when 20 wt % of ethanol (toxic material), 2.5 wt % of ethanol (toxic material), and 20 wt % of sorbitol (non-toxic material) are added to sub-mitochondrial particles and an electron donor to cause a reaction.
Figure 5B:
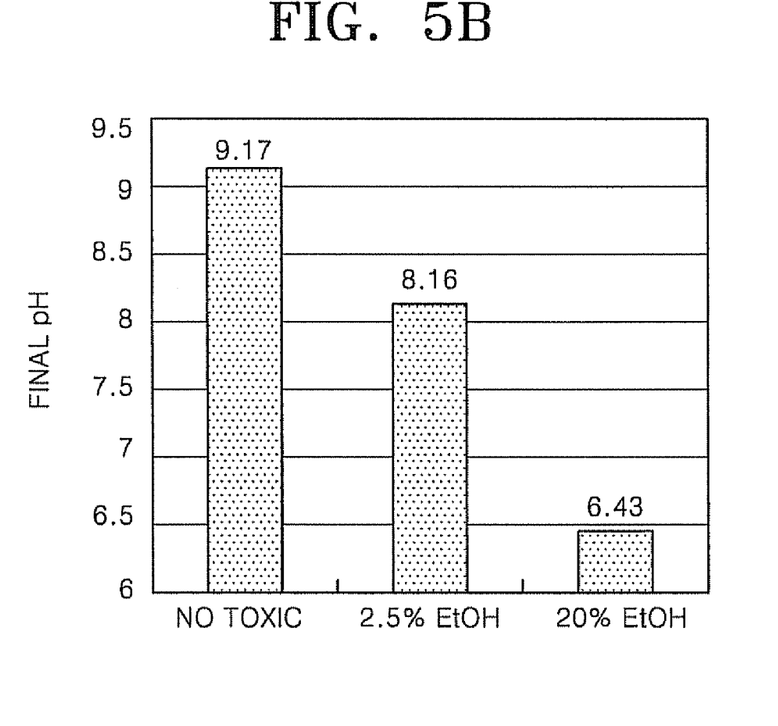
FIG. 5B is a graph showing the pH values of each reactant 10 minutes after the reaction described in FIG. 5A was initiated.

FIGS. 5A and 5B illustrate an exemplary embodiment of a method of positively detecting toxic materials in which phenolphthalein is used as a pH indicator. FIG. 5A is a graph illustrating pH values at two-minute intervals when 20 wt % of ethanol (toxic material), 2.5 wt % of ethanol (toxic material), and 20 wt % of sorbitol (non-toxic material) were added to sub-mitochondrial particles and an electron donor to cause reactions. FIG. 5B is a graph and showing the final pH value of each reactant after the reaction solutions were allowed to react for 10 minutes according to the reaction described in FIG. 5A.

Referring to FIGS. 5A and 5B, when high toxicity exists, pH starts at 6.4 and 10 minutes later, the pH of the reaction resultantbecomes 6.43 showing little change. When low toxicity exists, the pH of the reaction resultant increases to 8.16 and when non-toxicity exists, the pH of the reaction resultant rapidly increases to 9.17.

Using the result described above, after phenolphthalein, which is used as a pH indicator, is adjusted to various pH ranges, color changes may be identified by adding the phenolphthalein to the reaction resultants. Accordingly, toxic materials within a sample may be detected. The values calculated from the above process using phenolphthalein are illustrated in Table 3. The pH values of the reaction resultants having highly toxic materials, low toxic materials, and non-toxic materials are assumed to be 6.3, 8.3 and 9.3, respectively.

Referring to Table 3, when the initial pH value of phenolphthalein is adjusted to over 9, a signal (e.g., color after mixing) remains the same when there are no toxic materials and the signal changes when there are toxic materials, indicating a positive mechanism.

TABLE 3

| Adjusted pH | Color before mixing | Mixed with 1:1 | [H+] | pH | Color after mixing |
| --- | --- | --- | --- | --- | --- |
| pH 7 | Colorless | pH 7 + pH 6.3 (high toxicity) | $3.01 \times 10^{-7}$ | 6.52 | Colorless |
| | | pH 7 + pH 8.3 (low toxicity) | $5.25 \times 10^{-8}$ | 7.28 | Colorless |
| | | pH 7 + pH 9.3 (non-toxicity) | $5.03 \times 10^{-8}$ | 7.30 | Colorless |
| pH 8 | Colorless | pH 8 + pH 6.3 (high toxicity) | $2.56 \times 10^{-7}$ | 6.59 | Colorless |
| | | pH 8 + pH 8.3 (low toxicity) | $7.51 \times 10^{-9}$ | 8.12 | Colorless |
| | | pH 8 + pH 9.3 (non-toxicity) | $5.25 \times 10^{-9}$ | 8.28 | Colorless |

TABLE 3-continued

| Adjusted pH | Color before mixing | Mixed with 1:1 | [H$^+$] | pH | Color after mixing |
|---|---|---|---|---|---|
| pH 9 | Pink | pH 9 + pH 6.3 (high toxicity) | $2.51 \times 10^{-7}$ | 6.60 | Colorless |
| | | pH 9 + pH 8.3 (low toxicity) | $3.01 \times 10^{-9}$ | 8.52 | Colorless |
| | | pH 9 + pH 9.3 (non-toxicity) | $7.51 \times 10^{-10}$ | 9.12 | Pink |
| pH 10 | Pink | pH 10 + pH 6.3 (high toxicity) | $2.51 \times 10^{-7}$ | 6.60 | Colorless |
| | | pH 10 + pH 8.3 (low toxicity) | $2.56 \times 10^{-9}$ | 8.59 | Colorless |
| | | pH 10 + pH 9.3 (non-toxicity) | $3.01 \times 10^{-10}$ | 9.52 | Pink |
| pH 11 | Pink | pH 11 + pH 6.3 (high toxicity) | $2.51 \times 10^{-7}$ | 6.60 | Colorless |
| | | pH 11 + pH 8.3 (low toxicity) | $2.51 \times 10^{-9}$ | 8.60 | Colorless |
| | | pH 11 + pH 9.3 (non-toxicity) | $2.56 \times 10^{-10}$ | 9.59 | Pink |

Figure 6:
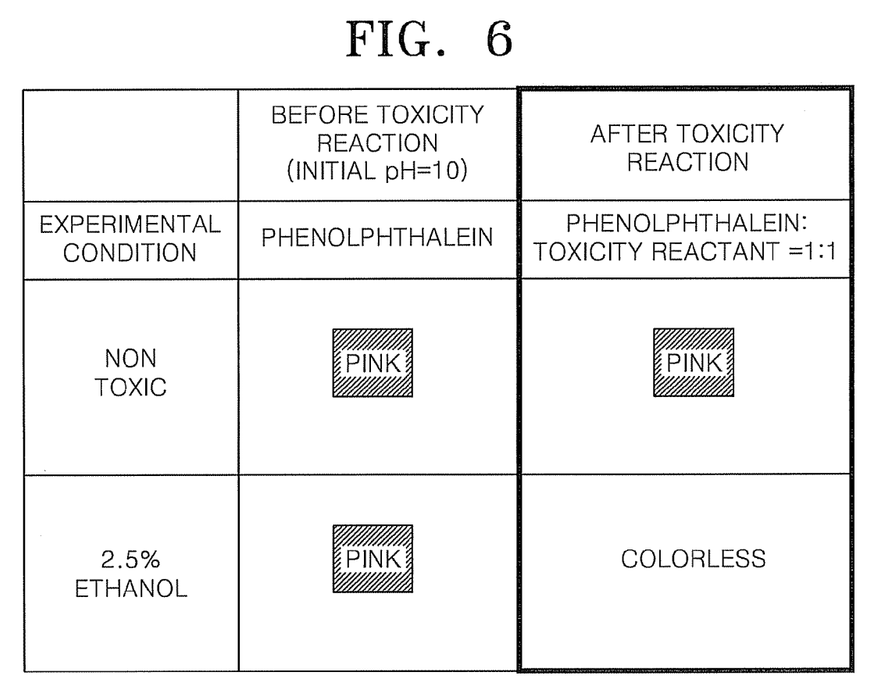
FIG. 6 is a diagram schematically illustrating another exemplary embodiment of a method of positively detecting toxic materials in which phenolphthalein is used as a pH indicator according to the present invention.

FIG. 6 is a diagram schematically illustrating an exemplary embodiment of a method of positively detecting toxic materials when phenolphthalein is used as a pH indicator. Referring to FIG. 6, after the pH of phenolphthalein was adjusted to 10 and mixed with the reaction resultant, the color did not change when toxic materials were not contained in the reaction resultant and the color changed even when low toxic materials of 2.5% of ethanol were contained in the reaction resultant.

When phenolphthalein is used, the presence of toxic materials can be positively detected. However, as shown above, as samples with low toxicity and high toxicity produce similar results the levels of toxicity level cannot be measured.

Figure 7:
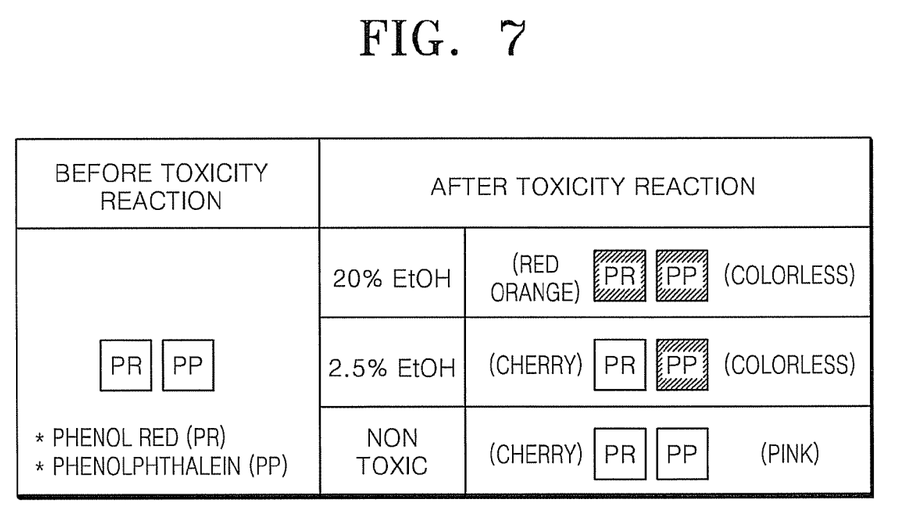
FIG. 7 is a diagram schematically illustrating another exemplary embodiment of a method of positively detecting toxic materials in which phenol red and phenolphthalein are used as pH indicators according to the present invention.

FIG. 7 is a diagram schematically illustrating an exemplary embodiment of a method of positively detecting toxic materials in which phenol red and phenolphthalein are used as pH indicators.

After the pH of each phenol red and phenolphthalein are adjusted to the fixed pH, they are added to the reaction resultant in order to identify the color changes.

Referring to FIG. 7, when toxic materials are not contained in the reaction resultant, the colors of both indicators did not change. When low toxic materials, e.g., 2.5 wt % of ethanol, were contained in the reaction resultant, the color of phenol red did not change while the color of phenolphthalein changed. When highly toxic materials, e.g., 20 wt % of ethanol, were contained in the reaction resultant, the colors of both phenol red and phenolphthalein may change.

As in the illustrated exemplary embodiments, when more than two pH indicators are used, the presence of toxic materials may be positively detected and the toxicity level may also be measured.

An exemplary embodiment of a kit for positive detection may detect various types of toxic materials and may measure the toxicity level thereof.

An exemplary embodiment of a kit for positively detecting toxic materials includes sub-mitochondrial particles having competent mitochondrial enzymes formed from inner membranes of mitochondria, an electron donor which transmits electrons to an electron transfer system of the sub-mitochondrial particles, and one or more pH indicators adjusting the pH thereof.

In exemplary embodiments, the sub-mitochondrial particle may be manufactured by sonicating whole mitochondria so that cristae transform to micelles.

In exemplary embodiments, the sub-mitochondrial particles may be lyophilized.

In exemplary embodiments, the mitochondrial enzymes may be formed of NADH-dehydrogenase, coenzyme-Q-cytochrome C reductase, and cytochrome C oxidase.

In exemplary embodiments, the electron donor may include at least one selected from a group consisting of NADH and NADPH.

In exemplary embodiments, the pH indicator may change color in the pH range of about 5.2 to 10.

In exemplary embodiments, the pH indicator may be selected from a group consisting of bromocresol purple, bromothymol blue, phenol red, thymolblue, and phenolphthalein.

In exemplary embodiments, the pH indicator may be adjusted in the pH range of about 7.5 to 10.

In exemplary embodiments, the pH indicator may be adjusted in the pH range of about 9 to 10.

In an exemplary embodiment of the kit, sub-mitochondria particles, competent mitochondrial enzymes, an electron donor, toxic materials, and one or more pH indicators adjusting the pH may be similar to those described as in the exemplary embodiments of the methods of detecting toxic materials discussed above.

Exemplary embodiments will now be described in greater detail with reference to the following examples. The following examples are for illustrative purposes and are not intended to limit the scope of the invention.

Example 1

Detecting Toxicity According to the Present Invention

Toxic materials are detected by using an exemplary method according to the present invention. Ethanol was used as a toxic material and sorbitol, which is known as a material having no toxicity to a cell, was used as a non-toxic material.

NaOH was adequately added to a pH indicator, phenol red, to adjust the pH to 10. Then, 20 wt % of sorbitol, 2.5 wt % of ethanol, and 20 wt % of ethanol were added to each 0.5 mg/ml of sub-mitochondrial particle ("SMP") (Havard Bioscience), 6 millimolar (mM) solution of NADH, and 50 mM of potassium chloride (KCl) were allowed to react for 10 minutes at ambient temperature. The reaction resultants obtained by the above process and a phenol red solution were mixed together with the weight ratio of 1:1 to identify the color of the mixture solution.

The results are shown in FIG. 4. Referring to FIG. 4, when 20 wt % of sorbitol (non-toxic material) and 2.5 wt % of ethanol (toxic material) were added, the mixture solution remained in a cherry-red color. However, when 20 wt % of ethanol (toxic material) was added, the color of the mixture solution changed to red-orange.

According to this result, phenol red may be used to positively detect a high toxicity level but may not be used to efficiently detect a low toxicity level.

Predictive Example 1

Detecting Toxicity According to the Present Invention

Toxic materials are detected in the same manner as in Example 1, except that phenolphthalein is used as a pH indicator instead of phenol red.

The results are shown in FIG. 6. Referring to FIG. 6, when 20 wt % of sorbitol (non-toxic material) is added, the mixture solution remains pink and while when 2.5 wt % of ethanol is added, the mixture solution loses its pink color and becomes colorless.

According to the result, phenolphthalein may be used to positively detect a low toxicity level but the toxicity level cannot be measured from the detection itself.

Predictive Example 2

Detecting Toxicity Level According to the Present Invention

Toxic materials are detected in the same manner as in Example 1, except that both phenol red and phenolphthalein are used as pH indicators instead of using phenol red alone.

The results are shown in FIG. 7. Referring to FIG. 7, when 20 wt % of sorbitol (non-toxic material) is added, the colors of two mixture solutions remain the same. When 2.5 wt % of ethanol (toxic material) is added, the color of the mixture solution in which phenol red is added remains the same while the mixture solution in which phenolphthalein is added loses its pink color and becomes colorless. When 20 wt % of ethanol (toxic material) is added, the colors of two mixture solutions in which phenol red and phenolphthalein are added change from cherry-red and pink to red-orange and colorless, respectively.

According to this result, when more than two kinds of pH indicators are used, toxic materials may be positively detected and a toxicity level also can be measured. "Measuring" the level of toxicity is considered as a comparative or discrete amount and/or type of color change indicating the level of toxicity.

As described above, exemplary embodiments of the method and kit according to the present invention allows detection of the presence of all kinds of toxic materials and measurement of the toxicity level thereof. Because no special equipment or apparatus is required for the method or kit, it is possible to simplify the method. When materials that are to be detected exist, the method according to the present invention is the same as the general positive detection mechanism and thus, commercialization is also possible.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A kit for positively detecting toxic materials within a sample, the kit comprising:
   sub-mitochondrial particles including enzymatically active enzymes involved in an electron transfer system of mitochondria;
   an electron donor which transmits electrons to the electron transfer system of the sub-mitochondrial particles; and
   a pH adjusted indicator, wherein the pH adjusted indicator is selected from the group consisting of bromocresol purple, bromothymol blue, phenol red, thymol blue and phenolphthalein and a pH of the pH adjusted indicator is a pH in the range of about 9 to 11.

2. The kit of claim 1, wherein the sub-mitochondrial particles are manufactured by sonicating whole mitochondria to transform cristae into micelles.

3. The kit of claim 1, wherein the sub-mitochondrial particles are lyophilized.

4. The kit of claim 1, wherein the mitochondrial enzyme is NADH-dehydrogenase, coenzyme-Q-cytochrome C reductase or cytochrome C oxidase.

5. The kit of claim 1, wherein the electron donor includes at least one selected from the group consisting of NADH and NADPH.

* * * * *